United States Patent
Buck

(10) Patent No.: US 10,539,595 B2
(45) Date of Patent: *Jan. 21, 2020

(54) SYSTEMS AND METHODS FOR IMPROVING THE RANGE OF SENSOR SYSTEMS

(71) Applicant: COVIDIEN LP, Mansfield, MA (US)

(72) Inventor: Dean C. Buck, Loveland, CO (US)

(73) Assignee: Covidien LP, Mansfield, MA (US)

( * ) Notice: Subject to any disclaimer, the term of this patent is extended or adjusted under 35 U.S.C. 154(b) by 245 days.

This patent is subject to a terminal disclaimer.

(21) Appl. No.: 15/651,784

(22) Filed: Jul. 17, 2017

(65) Prior Publication Data

US 2017/0315160 A1 Nov. 2, 2017

Related U.S. Application Data

(63) Continuation of application No. 14/721,763, filed on May 26, 2015, now Pat. No. 9,709,609.

(Continued)

(51) Int. Cl.
*G01R 19/165* (2006.01)
*A61B 18/12* (2006.01)
*A61B 18/00* (2006.01)

(52) U.S. Cl.
CPC .... *G01R 19/16571* (2013.01); *A61B 18/1206* (2013.01); *G01R 19/165* (2013.01);
(Continued)

(58) Field of Classification Search
CPC ............ G01R 19/16571; G01R 19/165; G01R 19/16576; G01R 19/0092; G01R 19/0084;
(Continued)

(56) References Cited

U.S. PATENT DOCUMENTS 3,369,549 A 2/1968 Armao
4,919,134 A 4/1990 Streeter
(Continued)

FOREIGN PATENT DOCUMENTS

WO 0009054 A1 2/2000
WO 0048670 A1 8/2000
WO 0066053 A1 11/2000

OTHER PUBLICATIONS

Extended European Search Report for EP 15 17 6402 dated Jan. 4, 2016.

*Primary Examiner* — Amy He

(57) ABSTRACT

A measurement circuit measures a waveform of electrical energy generated by a generator. The measurement circuit includes a sensor configured to sense a waveform having a first range of amplitudes, first and second circuits configured to filter the sensed waveform. Each circuit includes an attenuator configured to amplify an amplitude of the waveform by multiplying the waveform by an attenuation factor, an analog-to-digital converter (ADC) configured to digitally sample the amplified waveform, which has a second range of amplitudes, to obtain digital samples, a gain element configured to multiply the digital samples by a gain factor, and a factor adjustor configured to adjust the attenuation factor and the gain factor. The measurement circuit further includes a controller configured to calculate voltage and current of the waveform based on the digital samples and to control the generator based on the calculated voltage and current. The first range includes and is larger than the second range.

20 Claims, 9 Drawing Sheets

Related U.S. Application Data

(60) Provisional application No. 62/024,083, filed on Jul. 14, 2014.

(52) U.S. Cl.
CPC ............ *G01R 19/16576* (2013.01); *A61B 2018/0072* (2013.01); *A61B 2018/00666* (2013.01); *A61B 2018/00678* (2013.01); *A61B 2018/00767* (2013.01); *A61B 2018/00827* (2013.01); *A61B 2018/00892* (2013.01)

(58) Field of Classification Search
CPC ...... A61B 18/1206; A61B 2018/00678; A61B 2018/00827; A61B 2018/00666; A61B 2018/0072; A61B 2018/00892; A61B 2018/00767
USPC .................................... 324/76.11, 500, 522
See application file for complete search history.

(56) References Cited

U.S. PATENT DOCUMENTS

| | | | |
|---|---|---|---|
| 4,960,103 A | 10/1990 | Urso | |
| 4,962,761 A | 10/1990 | Golden | |
| 5,097,829 A | 3/1992 | Quisenberry | |
| 5,174,285 A | 12/1992 | Fontenot | |
| 5,211,631 A | 5/1993 | Sheaff | |
| 5,344,436 A | 9/1994 | Fontenot et al. | |
| 5,514,094 A | 5/1996 | Anello et al. | |
| 5,624,392 A | 4/1997 | Saab | |
| 5,645,531 A | 7/1997 | Thompson et al. | |
| 5,716,386 A | 2/1998 | Ward et al. | |
| 5,733,319 A | 3/1998 | Neilson et al. | |
| 5,837,003 A | 11/1998 | Ginsburg | |
| 5,871,526 A | 2/1999 | Gibbs et al. | |
| 5,957,963 A | 9/1999 | Dobak, III | |
| 5,965,089 A | 10/1999 | Jarvik et al. | |
| 5,972,013 A | 10/1999 | Schmidt | |
| 5,980,561 A | 11/1999 | Kolen et al. | |
| 6,019,783 A | 2/2000 | Philips et al. | |
| 6,042,559 A | 3/2000 | Dobak, III | |
| 6,051,019 A | 4/2000 | Dobak, III | |
| 6,096,068 A | 8/2000 | Dobak, III et al. | |
| 6,126,684 A | 10/2000 | Gobin et al. | |
| 6,146,411 A | 11/2000 | Noda et al. | |
| 6,149,670 A | 11/2000 | Worthen et al. | |
| 6,149,677 A | 11/2000 | Dobak, III | |
| 6,206,004 B1 | 3/2001 | Schmidt et al. | |
| 6,224,624 B1 | 5/2001 | Lasheras et al. | |
| 6,231,595 B1 | 5/2001 | Dobak, III | |
| 6,235,048 B1 | 5/2001 | Dobak, III | |
| 6,245,095 B1 | 6/2001 | Dobak, III et al. | |
| 6,251,129 B1 | 6/2001 | Dobak, III et al. | |
| 6,254,626 B1 | 7/2001 | Dobak, III et al. | |
| 6,261,312 B1 | 7/2001 | Dobak, III et al. | |
| 6,264,680 B1 | 7/2001 | Ash | |
| 6,287,326 B1 | 9/2001 | Pecor | |
| 6,290,717 B1 | 9/2001 | Philips | |
| 6,299,599 B1 | 10/2001 | Pham et al. | |
| 6,312,452 B1 | 11/2001 | Dobak, III et al. | |
| 6,338,727 B1 | 1/2002 | Noda et al. | |
| 6,375,674 B1 | 4/2002 | Carson | |
| 6,620,189 B1 | 9/2003 | Machold et al. | |
| 9,709,609 B2 * | 7/2017 | Buck | G01R 19/16571 |
| 2003/0117123 A1 | 6/2003 | Kimball et al. | |
| 2011/0213354 A1 | 9/2011 | Smith | |
| 2012/0265195 A1 | 10/2012 | Gilbert | |
| 2013/0057275 A1 | 3/2013 | Tamura et al. | |
| 2013/0267944 A1 | 10/2013 | Krapohl | |

\* cited by examiner

SYSTEMS AND METHODS FOR IMPROVING THE RANGE OF SENSOR SYSTEMS

CROSS-REFERENCE TO RELATED APPLICATIONS

This application is a continuation application of U.S. patent application Ser. No. 14/721,763, filed on May 26, 2015, which issued as U.S. Pat. No. 9,709,609 on Jul. 18, 2017, which claims the benefit of and priority to U.S. Provisional Application Ser. No. 62/024,083, filed on Jul. 14, 2014, the entire contents of which are incorporated by reference herein.

BACKGROUND

Technical Field

The present disclosure relates to improving the range of sensor systems. More particularly, the present disclosure relates to systems and methods for increasing the range of sensor systems for measuring voltage and current using a redundant sensor system configuration.

Background of Related Art

There are two common types of energy-based methods that are used to treat tissue: microwave surgery and electrosurgery. Both methods involve the application of high-frequency energy to cut or modify biological tissue by using an electrosurgical generator (also referred to as a power supply or waveform generator) that generates an alternating current (AC), which is applied to a patient's tissue through the active electrode or an antenna and is returned to the electrosurgical generator through the return electrode.

During energy-based treatments, the voltage and current waveforms of the electrosurgical energy generated by the electrosurgical generator are sensed by voltage and current sensors. The sensed voltage and current are sampled by analog-to-digital converters (ADCs) to obtain samples of the sensed voltage and current. A digital signal processor of the electrosurgical generator processes the samples to obtain voltage, current, power, and impedance measurements of the tissue being treated. The magnitudes of the voltage and current waveforms are then controlled based on one or more of these measurements and a desired power curve suitable for a particular electrosurgical procedure.

Electrosurgical generators typically include a redundant sensor system in addition to a main sensor system to ensure that the measurements of the main sensor system are accurate. The redundant sensor system is often used to periodically verify the measurements obtained by the main sensor system. In general, the main and redundant sensor systems include measurement circuitry, which inherently has a range of measurement values that it can reliably measure.

For example, the range of the measurement circuitry may be lower than the range of the voltages or currents to be measured. To address this issue, the measurement circuitry may offer different settings, e.g., high and low range settings. For the low range setting, the measurement circuitry readings are accurate over a low range of voltages or currents but not over a high range of voltages or currents. For the high range setting, the measurement circuitry readings are accurate over a high range of voltages and currents but not over a low range of voltages and currents. Thus, the range settings of the measurement circuitry need to be changed based on the measured voltage and current values.

SUMMARY

The present disclosure, in one aspect, features a processor that performs a method for controlling a system that includes a generator and an energy delivery device. The processor may be implemented by a field programmable gate array, an application specific integrated circuit, a digital signal processor, or a programmable digital signal processor.

In another aspect, the present disclosure features a measurement circuit that includes first and second circuits, a selecting circuit, a determination circuit, and a setting circuit. Each of the first and second circuits measures voltage or current generated by a generator. The selecting circuit selects the first circuit to provide the measured voltage or current. The determination circuit determines whether the measured voltage or current reaches a predetermined value, e.g., a predetermined voltage or current value. The setting circuit changes a setting of the second circuit from a first setting to a second setting when the determination circuit determines that the measured voltage or current reaches the predetermined value. The selecting circuit selects the second circuit to provide the measured voltage or current when a first predetermined time elapses after the setting circuit changes the setting of the second circuit. The setting circuit further changes a setting of the first circuit from the first setting to the second setting after the selecting circuit selects the second circuit.

The first and second circuits may include an attenuator that attenuates the voltage or current by an attenuation factor and a gain that multiplies the voltage or current by a gain factor to obtain the measured voltage or current. The attenuation factor for the first setting may be higher than the attenuation factor for the second setting, and the gain factor for the first setting may be lower than the gain factor for the second setting. Alternatively, the attenuation factor for the second setting may be lower than the attenuation factor for the second setting, and the gain factor for the first setting may be higher than the gain factor for the second setting. The setting circuit may set the attenuation factor and the gain factor. The product of the gain factor and the attenuation factor may be substantially one.

The selecting circuit may further select the first circuit to provide the measured voltage or current when a second predetermined time elapses after the setting circuit changes the setting of the first circuit.

The first predetermined time may be a time that allows for the measured voltage or current output from the second circuit to stabilize after the setting circuit changes the setting of the second circuit. The second predetermined time may be a time that allows for the measured voltage or current output from the first circuit to stabilize after the setting circuit changes the setting of the first circuit.

The measurement circuit may further include a calculation circuit that calculates a matching scale factor by dividing the measured voltage or current output from the first circuit by the measured voltage or current output from the second circuit, and a matching scale factor gain that multiplies the measured voltage or current output from the second circuit by the matching scale factor.

The measurement circuit may further include a calculation circuit that provides a measured voltage or current V according to the equation $V = V_c \times (1-x) + V_g \times x$, where $V_c$ is the measured voltage or current output from the first circuit, $V_g$ is the measured voltage or current output from the second circuit, x is $$\frac{t}{T}$$

for t=0 to t=T, and V=$V_g$ for t≥T, when switching from the measured voltage or current output from the first circuit to the measured voltage or current output from the second circuit.

The measurement circuit may further include a calculation circuit that provides a measured voltage or current V according to the equation V=$V_c$×x+$V_g$×(1−x), where $V_c$ is the measured voltage or current output from the first circuit, $V_g$ is the measured voltage or current output from the second circuit, x is $$\frac{t}{T}$$

for t=0 to t=T, and V=$V_c$ for t≥T, when switching from the measured voltage or current output from the second circuit to the measured voltage or current output from the first circuit.

When the determination circuit determines that the measured voltage or current reaches the predetermined value, the second circuit may stop providing the measured voltage or current during the first predetermined time.

The present disclosure, in another aspect, features a method for measuring voltage or current of electrical energy generated by a generator having a first circuit and a second circuit. The method includes measuring, at the first circuit, voltage or current of the generated electrical energy, measuring, at the second circuit, voltage or current of the generated electrical energy, selecting the first circuit to provide the measured voltage or current, determining whether the measured voltage or current reaches a predetermined value, changing a setting of the second circuit from a first setting to a second setting when it is determined that the voltage or current has reached the predetermined value, selecting the second circuit to provide the measured voltage or current when the first predetermined time elapses after changing the setting of the second circuit, and changing a setting of the first circuit from the first setting to the second setting after selecting the second circuit.

The present disclosure, in another aspect, features a generator that includes an output stage, a first circuit, a second circuit, a determination circuit, a setting circuit, and a selecting circuit. The output stage is coupled to a power source and generates electrical energy. The first circuit and the second circuit measure the voltage or current of the generated electrical energy. The selecting circuit selects the first circuit to provide the measured voltage or current. The determination circuit determines whether the measured voltage or current reaches a predetermined value.

The setting circuit changes a setting of the second circuit from a first setting to a second setting when the determination unit determines that the measured voltage or current reaches the predetermined value. The selecting circuit further selects the second circuit to provide the measured voltage or current when a first predetermined time elapses after the setting circuit changes the setting of the second circuit. The setting circuit further changes a setting of the first circuit from the first setting to the second setting after the selecting circuit selects the second circuit.

BRIEF DESCRIPTION OF THE DRAWINGS

Various embodiments of the present disclosure are described with reference to the accompanying drawings wherein.

DETAILED DESCRIPTION

An electrosurgical generator generates electrosurgical energy suitable to achieve a desired electrosurgical effect. It is desirable that the electrosurgical generator generates electrosurgical energy over a large range. During an electrosurgical procedure, sensors sense voltage and current waveforms and provide them to a measurement circuit. The measurement circuit measures the sensed voltage and current waveforms and a controller controls the output from the electrosurgical generator based on the measured voltage and current waveforms. For safety purposes, the electrosurgical generator has a redundant sensor system including at least two sensors (e.g., a main sensor and a redundant sensor) to sense the voltage and current waveforms.

Generally, a sensing system includes sensing elements, e.g., voltage and current sensors, and measurement elements or circuits, which include ADCs, for converting signals sensed by the sensing elements to measurement values. The measurement elements are located in the feedback of a control loop, and the settings of the ranges of the measurement elements are changed while the voltage and current waveforms are being measured to improve the range of the measurement elements.

During a transient period, the controller may change the range setting of the redundant measurement element, receive the measurement values output from the main measurement element, and control the magnitude of the voltage and current waveforms. After the transient period has elapsed, the controller may receive the measurement values output from the redundant measurement element, change the range setting of the main measurement element, and control the output from the electrosurgical generator based on the measurement values output from the redundant measurement element. In this way, the controller may continuously control the magnitude of the electrosurgical energy while avoiding discontinuities in measuring the voltage and current during the transient period so as to provide continuous control of the output from the electrosurgical generator.

The disclosed systems and methods for improving the range of the measurement elements may be employed in any type of electronic device that incorporates redundant sensing elements. For example, the systems and methods of the present disclosure may be employed in energy-based medical devices. For purposes of illustration, and in no way limiting the scope of the appended claims, the systems and methods for improving the range of measurement elements are described in the present disclosure in the context of electrosurgical systems.

Figure 1:
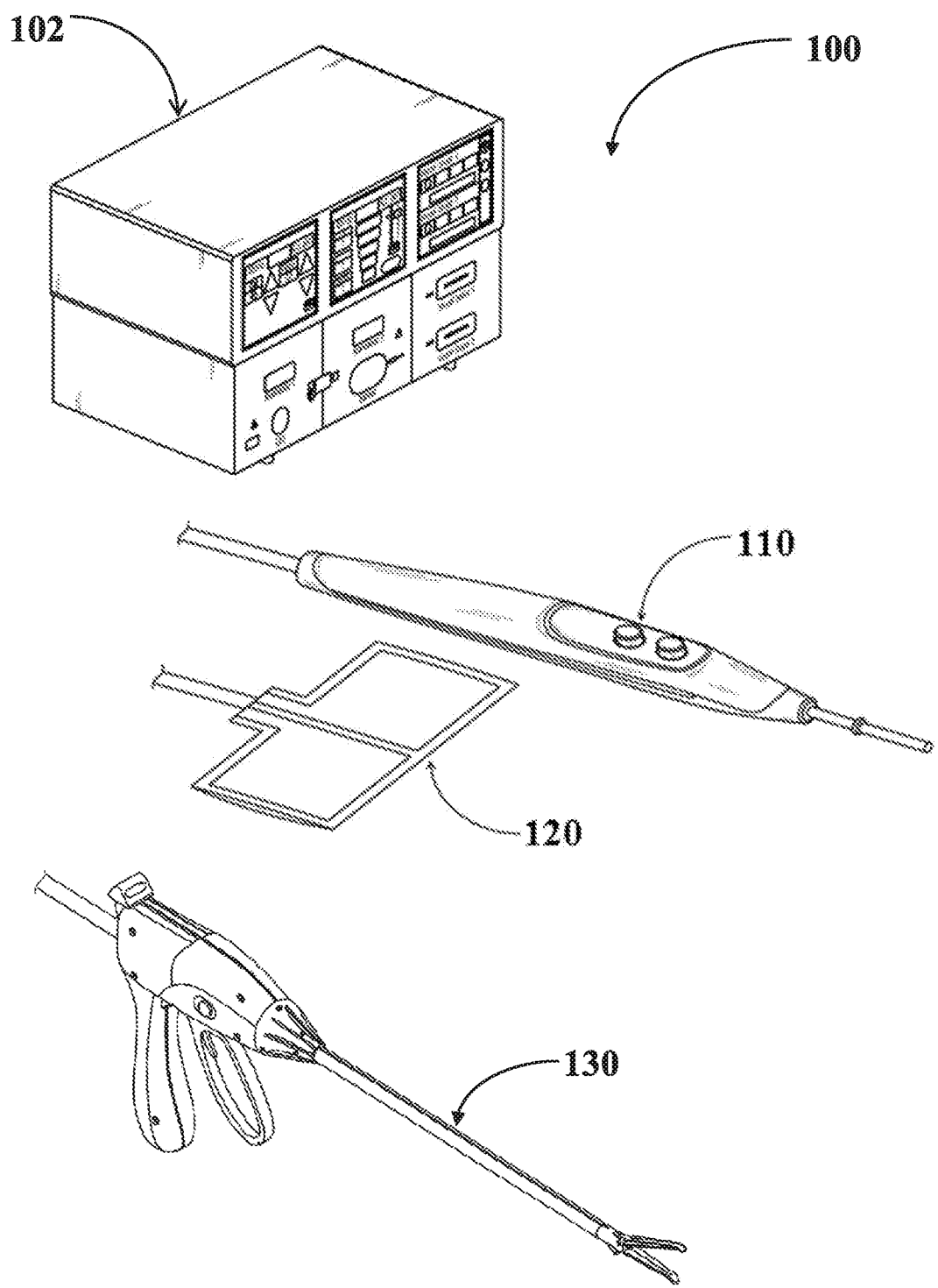
FIG. 1 is an illustration of an electrosurgical system in accordance with embodiments of the present disclosure.

FIG. 1 illustrates an electrosurgical system 100 in accordance with embodiments of the present disclosure. The electrosurgical system 100 includes an electrosurgical generator 102 which generates electrosurgical energy to treat tissue of a patient. The electrosurgical generator 102 generates an appropriate level of electrosurgical energy based on the selected mode of operation (e.g., cutting, coagulating, ablating, or sealing) and/or the sensed voltage and current waveforms of the electrosurgical energy. The electrosurgical generator 102 may also include a plurality of output connectors corresponding to a variety of energy delivery devices, e.g., electrosurgical instruments.

The electrosurgical system 100 further includes a number of energy delivery devices. For example, the electrosurgical system 100 includes monopolar electrosurgical instrument 110 having an electrode for treating tissue of the patient (e.g., an electrosurgical cutting probe or ablation electrode, also known as an electrosurgical pencil) with a return pad 120. The monopolar electrosurgical instrument 110 can be connected to the electrosurgical generator 102 via one of the plurality of output connectors. The electrosurgical generator 102 may generate electrosurgical energy in the form of radio frequency (RF) energy. The electrosurgical energy is supplied to the monopolar electrosurgical instrument 110, which applies the electrosurgical energy to treat the tissue. The electrosurgical energy is then returned to the electrosurgical generator 102 through the return pad 120. The return pad 120 provides sufficient contact area with the patient's tissue so as to minimize the risk of tissue damage due to the electrosurgical energy applied to the tissue.

The electrosurgical system 100 also includes a bipolar electrosurgical instrument 130. The bipolar electrosurgical instrument 130 can be connected to the electrosurgical generator 102 via one of the plurality of output connectors. The electrosurgical energy is supplied to one of the two jaw members of the bipolar electrosurgical instrument 130, is applied to treat the tissue, and is returned to the electrosurgical generator 102 through the other of the two jaw members.

The electrosurgical generator 102 may be any suitable type of generator and may include a plurality of connectors to accommodate various types of electrosurgical instruments (e.g., a monopolar electrosurgical instrument 110 and a bipolar electrosurgical instrument 130). The electrosurgical generator 102 may also be configured to operate in a variety of modes, such as ablation, cutting, coagulation, and sealing. The electrosurgical generator 102 may include a switching mechanism (e.g., relays) to switch the supply of RF energy among the connectors to which various electrosurgical instruments may be connected. For example, when the monopolar electrosurgical instrument 110 is connected to the electrosurgical generator 102, the switching mechanism switches the supply of RF energy to the monopolar plug. In embodiments, the electrosurgical generator 102 may be configured to provide RF energy to a plurality of instruments simultaneously.

The electrosurgical generator 102 includes a user interface having suitable user controls (e.g., buttons, activators, switches, or touch screens) for providing control parameters to the electrosurgical generator 102. These controls allow the user to adjust parameters of the electrosurgical energy (e.g., the power level or the shape of the output waveform) so that the electrosurgical energy is suitable for a particular surgical procedure (e.g., coagulating, ablating, tissue sealing, or cutting). The electrosurgical instruments 110 and 130 may also include a plurality of user controls. In addition, the electrosurgical generator 102 may include one or more display screens for displaying a variety of information related to operation of the electrosurgical generator 102 (e.g., intensity settings and treatment complete indicators).

Figure 2:
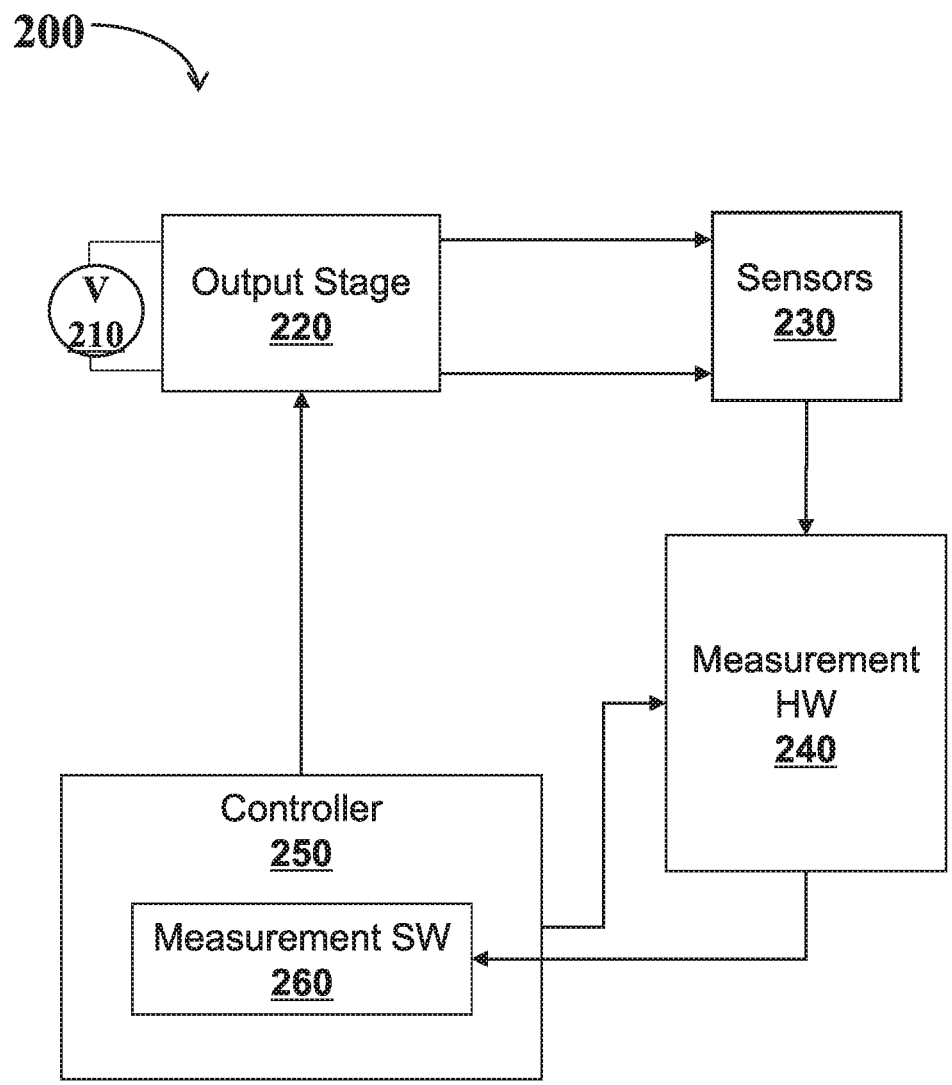
FIG. 2 is a block diagram of generator circuitry of the electrosurgical generator of FIG. 1.

FIG. 2 is a block diagram of generator circuitry 200 of the electrosurgical generator 102 of FIG. 1. The generator circuitry 200 includes an output stage 220, sensors 230, measurement hardware 240, and a controller 250. The electrosurgical generator 102, by way of the generator circuitry 200, is configured to connect to an alternating current (AC) power source 210, such as a wall power outlet or other power outlet, which generates AC having a low frequency (e.g., 25 Hz, 50 Hz, or 60 Hz). The AC power source 210 provides AC power to the output stage 220 which converts the low frequency AC to an AC having a frequency suitable for an electrosurgical procedure (e.g., microwave or radio frequencies). During the conversion from low frequency AC to high frequency AC, the output stage 220 may convert the low frequency AC to direct current (DC) and then invert the DC to the high frequency AC.

The appropriate frequency for the electrosurgical energy may differ based on electrosurgical operations and modes of electrosurgery. For example, nerve and muscle stimulations cease at about 100,000 cycles per second (100 kHz) above which point some electrosurgical procedures can be performed safely; i.e., the electrosurgical energy can pass through a patient to targeted tissue with minimal neuromuscular stimulation. For example, typically ablation procedures use a frequency of 472 kHz. Other electrosurgical procedures may be performed at frequencies lower than 100 kHz, e.g., 29.5 kHz or 19.7 kHz, with minimal risk of damaging nerves and muscles.

The output stage 220 may output AC signals with various frequencies suitable for electrosurgical procedures. The output stage 220 is electrically coupled to an energy delivery device which may be a bipolar electrosurgical instrument 130 or a monopolar electrosurgical instrument 110 of FIG. 1, which treats tissue with the electrosurgical energy.

In embodiments, the AC power source 210 may be replaced by a battery that supplies DC power. The output stage 220 may then directly convert the DC power to high frequency AC suitable to achieve a desired electrosurgical effect.

The plurality of sensors 230 sense voltage and current waveforms at the output of the output stage 220 before being supplied to the monopolar electrosurgical instrument 110, which is shown in FIG. 1. The plurality of sensors 230 may include main and redundant sensors for sensing voltage and current waveforms. This redundancy feature ensures the reliability, accuracy, and stability of the voltage and current measurements at the output of the output stage 220.

In embodiments, the plurality of sensors 230 may include fewer or more sets of voltage and current sensors depending on the application or the design requirements. The plurality of sensors 230 may measure the voltage and current waveforms at the output of the output stage 220 and from other components of the generator circuitry 200 such as an inverter and a resonant matching network (not shown). The plurality of sensors 230 may include any known technology for sensing voltage and current including, for example, a Rogowski coil for sensing current.

While each of the plurality of sensors 230 may be able to sense a full dynamic range of voltage or current waveforms, the measurement hardware 240 may not be able to measure the full dynamic range of voltage and current waveforms sensed by the plurality of sensors 230. Thus, the measurement hardware 240 may include at least two different range settings, e.g., a high range setting and low range setting, because the dynamic range of any one range setting of the measurement hardware 240 may be smaller than the dynamic range of the voltage and current waveforms generated by the output stage 220. For the low range setting, measurements by the measurement hardware 240 are accurate at low voltage or current values but are not accurate at high voltage or current values. For the high range setting, measurements are accurate at high voltage or current values but are not accurate at low voltage or current values because the noise floor of the measurement hardware 240 degrades the accuracy of the measurements at low voltage or current values. For these reasons, a range setting of the measurement hardware 240 is changed between the low range setting and the high range setting. In some embodiments, the range setting may be changed between three or more range settings based upon the characteristics of the sensors.

During the transition from one range setting to another, a transient period is needed to allow for the voltage and current measurement values to stabilize. Typically, electrosurgical systems do not perform control during the transient period. Thus, switching from one range setting to another may create an unwanted discontinuity in the control process and may cause harm to the patient due to the absence of power control. The present disclosure provides nearly instantaneous switching between range settings so as to reduce the possibility of causing harm.

Figure 4:
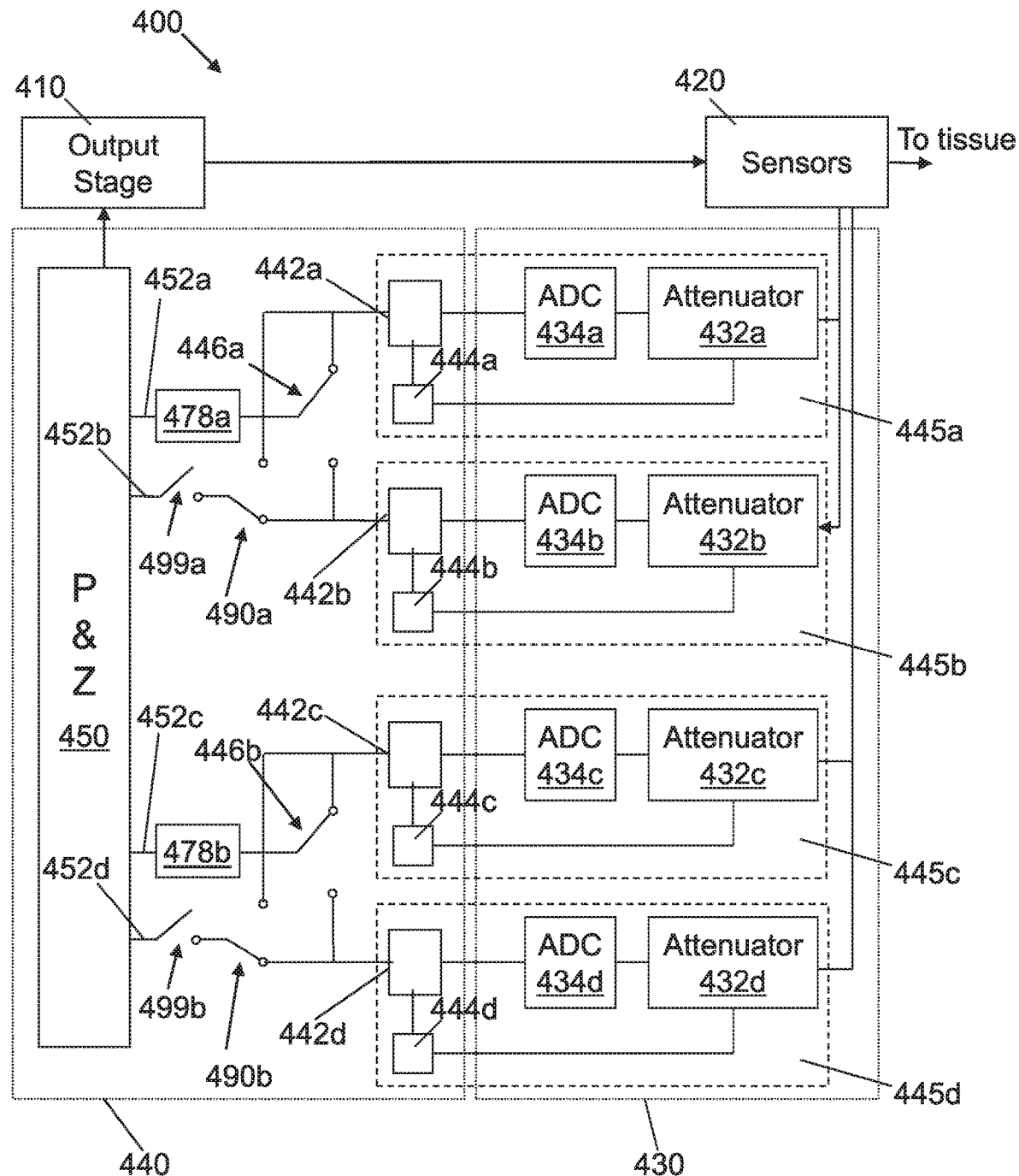
FIG. 4 is a schematic block diagram of the generator circuitry and measurement circuitry in accordance with some embodiments of the present disclosure.

The sensed voltage and current waveforms are provided to the measurement hardware 240 that converts analog voltage and current waveforms into digital voltage and current waveforms by using analog-to-digital converters (ADCs), examples of which are shown in FIG. 4. The ADCs sample the sensed voltage and current waveforms to obtain digital samples of the voltage and current waveforms generated by the output stage 220. The ADCs may be configured to sample outputs of the sensors 230 at a sampling frequency that is an integer multiple of the frequency of the generated electrosurgical energy.

The ADCs may sample only a fixed range of magnitudes of an analog signal. Thus, when the magnitudes of the sensed voltage and current waveforms are higher than the fixed range of magnitudes, the measurement hardware 240 may reduce the magnitudes of the sensed voltage and current waveforms to the fixed range of magnitudes before sampling the sensed voltage and current waveforms and then increase the magnitudes of the voltage and current samples to compensate for the reduction of the magnitudes after the ADC samples the sensed voltage and current waveforms. In other embodiments, the measurement hardware 240 may reduce the magnitudes of the sensed voltage and current waveforms to the fixed range of magnitudes before sampling the sensed voltage and current waveform, and then the software executed in the controller 250 may increase the magnitudes of the voltage and current samples.

When the magnitudes of the sensed voltage and current waveforms are lower than the fixed range of magnitudes of the ADCs, the measurement hardware 240 may include features that increase the magnitudes of the sensed voltage and current waveforms to the fixed range of magnitudes before sampling the sensed voltage and current waveforms and then reduce the magnitudes of the digital samples to compensate for the increase of the magnitudes. In this way, the sensors 230 can sense the full range of the signal output from the electrosurgical generator from the lower value output to the upper value output. The full range of the output signal, however, may not fit within the fixed input range of the ADCs. The controller 250 according to the present disclosure may change the range settings of the measurement hardware 240 so that it properly measures or samples the full range of the output signal sensed by the sensors 230.

The controller 250 receives the digital samples of the sensed voltage and current waveforms from the measurement hardware 240 to generate a control signal which is provided to the output stage 220 to control the output of the output stage 220. In particular, the digital samples from the measurement hardware 240 are processed by the measurement software 260 to obtain control parameters and the controller 250 uses the control parameters of the measurement software 260 to generate a control signal to control the output stage 220.

The measurement software 260 may further process the digital samples to calculate RMS voltage and current values of the generated electrosurgical energy and to calculate average power and/or impedance of the tissue being treated. The measurement software 260 provides the control parameters (e.g., the voltage and current values, the average power, and the impedance of the tissue) to the controller 250. The controller 250 may then control the output stage 220 based on the average power and/or the impedance of the tissue by comparing them with a power-impedance profile specific to an electrosurgical procedure, e.g., ablation. For example, when the average power is lower than the power of the power-impedance profile at a specific impedance of the tissue, the controller 250 generates a control signal that causes the output stage 220 to increase the power of the generated electrosurgical energy.

In embodiments, the controller 250 may further change the range settings of the measurement hardware 240. When the controller 250 measures the voltage and current values, the controller 250 determines whether the measured voltage and current values have reached a threshold value indicating that the range setting of the measurement hardware 240 should be changed to accommodate the dynamic range of the sensed voltage and current waveforms. If it is determined that the voltage and current measured values have reached the threshold value, the controller 250 provides a control signal to the measurement hardware 240 so that the measurement hardware 240 changes its range settings from the low range setting to the high range setting.

In embodiments, the controller 250 including the measurement software 260 may be implemented in a digital signal processor (DSP), application-specific integrated circuit (ASIC), field-programmable gate array (FPGA), or different types of programmable read-only memory (e.g., PROM, EPROM, EEPROM, etc.).

Figure 3A:
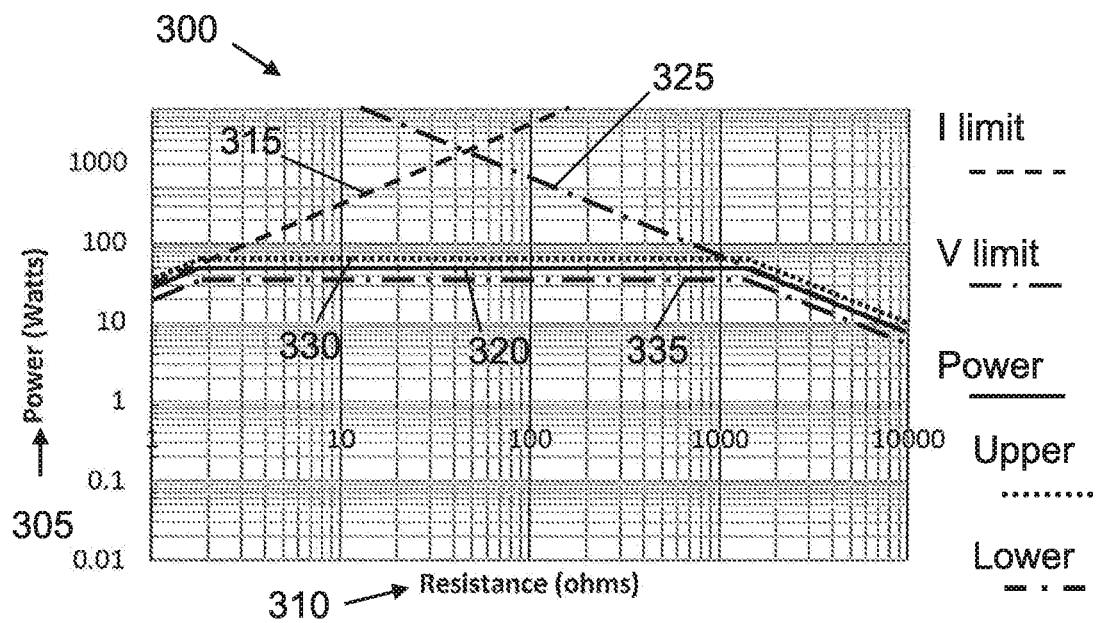
FIG. 3A is a graph illustrating a desired power curve and its upper and lower power tolerance limits if the measurement devices for measuring power were within tolerance limits across their entire operating range.

FIG. 3A is a graph 300 illustrating a desired power curve 320 for a specific power setting of the electrosurgical generator 102. The desired power curve 320 is defined by a maximum current limit 315 and a maximum voltage limit 325. As shown in FIG. 3A, the graph 300 includes two axes: vertical axis 305 representing power in watts and horizontal axis 310 representing tissue impedance in ohms. FIG. 3A also shows a tolerance range defined by upper and lower power tolerance limits 330 and 335 with respect to the desired power curve 320 if the measurement devices for measuring power were within tolerance limits across their entire operating range.

Figure 3B:
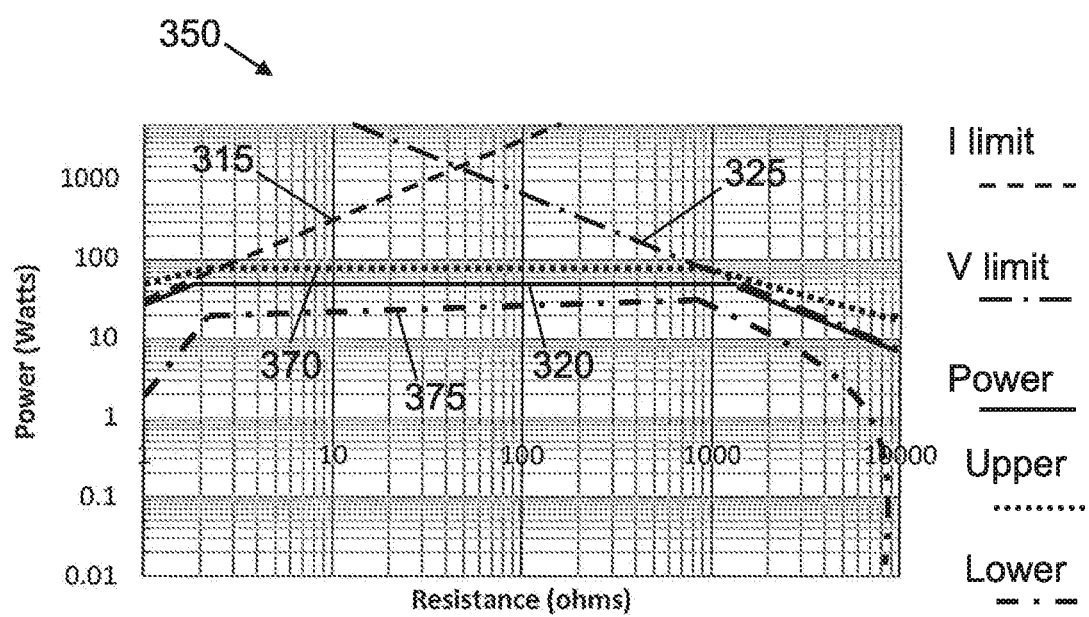
FIG. 3B is a graph illustrating upper and lower power tolerance limits with respect to the desired power curve of FIG. 3A when the measurement devices are within tolerance limits only at a high portion of their entire operating range.

FIG. 3B is a graph 350 illustrating upper and lower power tolerance limits 370 and 375 with respect to the desired power curve 320 of FIG. 3A when the measurement devices for measuring power are within tolerance limits only at a high portion of their entire operating range.

Specifically, the power tolerance limits between 2 ohms and 1000 ohms show that the measurement circuitry provides a reasonable level of accuracy. However, the power tolerance limits outside that range show a decrease in the accuracy of the measurements. In other words, the measurement circuitry has a limited dynamic range. For this reason, different range settings of the measurement circuitry need to be selected depending on the different levels of voltage or current measured by the measurement circuitry. Thus, for the entire range of resistance, settings of the measurement circuitry are changed based on the measurement values of the voltage and current.

For example, during an electrosurgical procedure, the operating point (OP) could go from a low impedance, e.g., 1 ohm, to a high impedance, e.g., 5000 ohms. At the low impedance OP the current is high and the voltage is low. Thus, to minimize measurement errors resulting from the limited dynamic range of the measurement circuitry, the current measurement circuitry is set to its high range setting and the voltage measurement circuitry is set to its low range setting. At the high impedance OP, the current is low and the voltage is high. Thus, to minimize measurement errors, the current measurement circuitry is set to its low range setting and the voltage measurement circuitry is set to its high range setting. In summary, the range settings of the voltage and current measurement circuitry are changed depending on the different operating points. That is, during the electrosurgical procedure, the range setting of the current measurement circuitry changes from high to low and the range setting of the voltage measurement circuitry changes from low to high.

Even though the sensors 230 of FIG. 2 can accommodate the full dynamic range of the voltage and current waveforms, the measurement hardware 240 having a single range setting may not span the dynamic ranges of the voltage and current waveforms. The noise floor of the measurement hardware 240 prevents the error from remaining within a scale factor, i.e., a percentage tolerance. For these reasons, the range settings of the measurement hardware 240 may be changed during the electrosurgical procedure to meet certain measurement tolerance levels.

FIG. 4 is a schematic block diagram 400 of the generator circuitry of FIG. 2, which obtains continuous measurements of sensed voltage and current waveforms according to some embodiments of the present disclosure. The schematic block diagram 400 includes an output stage 410, sensors 420, measurement hardware 430, and measurement software 440. The output stage 410 generates and outputs an electrosurgical signal having an appropriate frequency for treating tissue. The sensors 420 are disposed between the output stage 410 and the tissue (not shown) to sense the voltage and current waveforms of the electrosurgical energy output from the output stage 410. The sensed voltage and current waveforms are provided to the measurement hardware 430 that converts the sensed voltage and current waveforms to digital samples. The measurement software 440 receives the digital samples and processes them to obtain control parameters. The controller 250 (FIG. 2), which includes the measurement software 440, then generates a control signal to control the output stage 410 to generate appropriate electrosurgical energy suitable for surgical purposes, based on the control parameters.

The measurement hardware 430 may include attenuators 432a and 432b for attenuating the sensed voltage waveforms, attenuators 432c and 432d for attenuating the sensed current waveforms, ADCs 434a and 434b for the sensed voltage waveforms, and ADCs 434c and 434d for the sensed current waveforms. The number of attenuators and ADCs corresponds to the number of voltage and current sensors. For illustration purposes only, four attenuators and four ADCs corresponding to the voltage and current waveforms sensed by the sensors 420 (e.g., two voltage sensors and two current sensors) are shown in FIG. 4.

The attenuators 432a, 432b and the ADCs 434a, 434b for the sensed voltage waveforms are described here and similar descriptions may be applied to the attenuators 432c, 432d and the ADCs 434c, 434d for the sensed current waveforms. The attenuator 432a receives a sensed voltage waveform from a main sensor among a plurality of voltage sensors and the attenuator 432b receives a sensed voltage waveform from a redundant sensor among the plurality of voltage sensors. The attenuators 432a and 432b reduce the magnitudes of the sensed voltage waveforms by an attenuation factor so that the sensed voltage waveforms are within the dynamic range of the ADCs 434a and 434b. The ADCs 434a and 434b sample the attenuated sensed voltage waveforms at a desired frequency, which may be an integer multiple of the frequency of the sensed voltage waveforms. The digital samples of the sensed voltage waveforms are then provided to the measurement software 440.

The measurement software 440 processes the digital samples to obtain measurements of the voltage and current values, power, and tissue impedance. The measurement software 440 includes gains 442a, 442b, factor adjustors 444a, 444b, main voltage selector 446a, and redundant voltage selector 490a for the sensed voltage waveforms. The measurement software 440 also includes gains 442c, 442d, factor adjustors 444c, 444d, main current selector 446b, and redundant current selector 490b for the sensed current waveforms. The measurement software 440 further includes calculator 450, voltage switch 499a, current switch 499b, voltage matching scale factor gain block 478a, and current matching scale factor gain block 478b. The measurement software 440 receives samples of the voltage and current waveforms from the ADCs 434a-434d. The gains 442a and 442b receive the sampled voltage waveforms and multiply them by a gain factor to compensate for the reduction of the signal by the attenuators 432a and 432b respectively. In embodiments, gains 442a-442d, factor adjustors 444a-444d, main voltage selector 446a, and/or main current selector 446b may be implemented by firmware and/or hardware. As used in the present disclosure, the term selecting circuit may refer software and/or hardware used to implement the main selectors 446a and 446b.

The factor adjustors 444a and 444b adjust the attenuation factors and the gain factors so that the product of the attenuation factor and the corresponding gain factor are equal to one. In this way, the actual magnitude of the sensed voltage waveform is maintained before and after digitization of the analog voltage waveform.

The main voltage measurement circuit 445a includes the attenuator 432a, the ADC 434a, the gain 442a, and the factor adjustor 444a, and the redundant voltage measurement circuit 445b includes the attenuator 432b, the ADC 434b, the gain 442b, and the factor adjustor 444b. Thus, the voltage measurement circuitry includes the main voltage measurement circuit 445a and the redundant voltage measurement circuit 445b. In the same way, the main current measurement circuit 445c includes the attenuator 432c, the ADC 434c, the gain 442c, and the factor adjustor 444c, and the redundant current measurement circuit 445d includes the attenuators 432d, the ADC 434d, the gain 442d, and the factor adjustors 444d. Thus, the current measurement circuitry includes the main current measurement circuit 445c and the redundant current measurement circuit 445d. In other words, the main measurement circuitry includes the main voltage measurement circuit 445a and the main current measurement circuit 445c, and the redundant measurement circuitry includes the redundant voltage measurement circuit 445b and the redundant current measurement circuit 445d.

For example, in some embodiments, the controller 250 may change the range settings of the redundant measurement circuits 445b and 445d from the low range setting to the high range setting but may maintain the range settings of the main measurement circuits 445a and 445c at the low range setting. In other embodiments, the controller 250 may change range settings of the sensors 420 or both the sensors 420 and the measurement hardware 430.

In embodiments, the calculator 450, which may be a logic circuit or a microcontroller having a processor for executing a program stored in memory of the microcontroller, receives measurement values (i.e., digital samples) of the sensed voltage and current waveforms from the measurement circuits 445a-d. The main voltage selector 446a selects between the main voltage measurement circuit 445a and the redundant voltage measurement circuit 445b to obtain main voltage measurement values, which are provided to the calculator 450 via the main voltage measurement channel 452a. Similarly, the main current selector 446b may select between the main current measurement circuit 445c and the redundant current measurement circuit 445d to provide main current measurement values to the calculator 450 via a main current measurement channel 452c.

When the measurement values from the main measurement circuits 445a and 445c reach a predetermined level, the range settings of the redundant measurement circuits 445b and 445d are changed, e.g., from low range settings to high range settings, and the calculator 450 waits a first transient period for the measurement values of the redundant measurement circuits 445b and 445d to stabilize. The calculator 450 also sends control signals to the switches 499a and 499b to open the switches 499a and 499b, which disconnects the redundant measurement channels 452b and 452d from the redundant measurement circuit 445b and 445d, respectively, so that the calculator 450 does not receive redundant measurement values through the redundant measurement channels 452b and 452d.

After the first transient period has elapsed, the main selectors 446a and 446b select the outputs of the redundant measurement circuits 445b and 445d so that the calculator 450 can receive main measurement values from the redundant measurement circuits 445b and 445d, which are operating according to the changed range settings, via the main measurement channels 452a and 452c, respectively.

Next, the range settings of the main measurement circuits 445a and 445c are changed, e.g., from low range settings to high range settings, and the calculator 450 waits a second transient period for the outputs of the main measurement circuits 445a and 445c to stabilize. In some embodiments, since the measurement values of the main measurement circuits 445a and 445c are not stable, the switches 499a and 499b are maintained in an open state during the second transient period so that the calculator 450 does not receive redundant measurement values output from the main measurement circuits 445a and 445c via the redundant measurement channels 452b and 452d, respectively.

After the second transient period has elapsed, the calculator 450 sends control signals to the switches 499a and 499b to close the switches 499a and 499b, which connects the redundant measurement channels 452b and 452d to the main measurement circuits 445a and 445c, respectively, so that the calculator 450 receives redundant measurement values from the main measurement circuits 445a and 445c via the redundant measurement channel 452b and 452d, respectively.

Thus, as described above, the main and redundant measurement circuits 445a-445d may reverse roles in the process of changing range settings, i.e., the main measurement circuits 445a and 445c may become providers of redundant measurement values and the redundant measurement circuits 445b and 445d may become providers of main measurement values. The main and redundant measurement circuits 445a-445d may remain in these new roles until the range settings of the measurement circuits 445a and 445c need to be changed again. In this way, the calculator 450 can continuously receive main measurement values while the range settings of the measurement circuits 445a-d are being changed to accommodate sensed voltage and current waveforms having a wide dynamic range.

In other embodiments, after the first transient period has elapsed, the redundant selectors 490a and 490b may not switch from the outputs of redundant measurement circuits 445b and 445d to the outputs of the main measurement circuits 445a and 445c, respectively. Also, after the second transient period has elapsed, the main selectors 446a and 446b may be switched back to the main measurement circuits 445a and 445c so that the calculator 450 receives main measurement values from the main measurement circuits 445a and 445c via the main measurement channels 452a and 452c. Furthermore, after the second transient period has elapsed, the calculator 450 may send a control signal to the switches 499a and 499b, which connects the redundant measurement channels 452b and 452d to the redundant measurement circuits 445b and 445d respectively, so that the calculator 450 receives redundant measurement values from the redundant measurement circuits 445b and 445d via the redundant measurement channel 452b and 452d, respectively. In this way, the main measurement circuits 445a and 445c may return to their roles as providers of main measurement values and the redundant measurement circuits 445b and 445d may maintain their roles as providers of redundant measurement values.

In embodiments, the gains 442a and 442b and the factor adjustors 444a and 444b may be implemented in hardware so that the gains 442a and 442b and the factor adjustors 444a and 444b can be a part of the measurement hardware 430.

The calculator 450 receives main and redundant measurement values and processes them to calculate root mean square (RMS) voltage and current values, power, tissue impedance, etc. The controller 250 (FIG. 2), which includes the measurement software 440, then generates a control signal and provides it to the output stage 410 so that an appropriate electrosurgical signal can be generated to treat tissue. The controller 250 may generate other control signals to cause the factor adjustors 444a and 444b to change the gain factor settings in the attenuators 432a and 432b, when the calculated voltage and/or current values reach a threshold value. In this way, the controller 250 can change the range settings of the measurement hardware 430.

The voltage matching scale factor gain block 478a is located between the main voltage selector 446a and the main voltage measurement channel 452a, and the current matching scale factor gain block 478b is located between the main current selector 446b and the main current measurement channel 452c. As described in more detail below, these matching scale factor gain blocks 478a and 478b adjust the main measurement values to account for differences between main measurement values output from the main measurement circuits 445a and 445c and main measurement values output from the redundant measurement circuits 445b and 445d when switching between these circuits.

In embodiments, the controller 250 may generate control signals to change the range settings of the voltage measurement circuitry separately from the range settings of the current measurement circuitry. In other words, the controller 250 may change the range settings of the voltage measurement circuitry at the same time or at a different time from when it changes the range settings of the current measurement circuitry. Thus, when the current measurement value reaches a certain value, the controller generates a current control signal for the current measurement circuitry to change a range setting of the current measurement circuitry to another range setting, and, when the voltage measurement value reaches a certain value, the controller 250 generates a voltage control signal for the voltage measurement circuitry to change a range setting of the voltage measurement circuitry to another range setting.

When the range setting of the voltage or current measurement circuitry is changed, the corresponding attenuation and gain factors may be changed. For example, when the controller 250 changes the range settings of the voltage measurement circuits 445a and 445b, the controller 250 further controls the voltage factor adjustors 444a and 444b to adjust the attenuation factors of the attenuators 432a and 432b and the gain factors of the gains 442a and 442b.

The following description is an example showing how the voltage sensors, attenuators, ADCs, gains, and factor adjustors are operated and controlled. The ADCs may be configured to sample signals having a maximum magnitude of 1 volt (V) and, when the ADCs receive an input of 1 V, the ADCs may output 1024 counts. A voltage sensor may be designed to sense a signal having a maximum magnitude of 100 V based on the voltage sensor's settings and capabilities. Thus, the attenuation factor is set to $1/100$ to convert a signal having a maximum magnitude of 100 V to 1 V so that the sensed voltage waveform can be sampled by an ADC, and the gain factor is set to 100 to convert 1 V to 100 V.

Thus, when the voltage sensor senses a voltage waveform having a magnitude of 78.125 V, an attenuator (e.g., the attenuator 432a of FIG. 4) multiplies the magnitude of the sensed voltage waveform by an attenuation factor, e.g., $1/100$, so that the magnitude of the voltage waveform is reduced to 0.78125 V. An ADC (e.g., the ADC 434a of FIG. 4) then outputs 800 counts which correspond to 0.78125 V. A gain element (e.g., the gain 442a of FIG. 4) then multiplies the output of the ADC by a gain factor, e.g., 100, to obtain 78.125 V.

When the dynamic range of the voltage sensor allows the voltage sensor to sense a signal having a maximum magnitude of 1000 V, then the attenuation factor is set to $1/1000$ and the gain factor is set to 1000 by the voltage adjustor. With this wide dynamic range, when the voltage sensor senses 78.125 V, the attenuator multiplies 78.125 V by $1/1000$ and the ADC outputs 80 counts, which correspond to 0.078125 V. The gain then multiplies 0.078125 V by 1000 to obtain 78.125V. Thus, the attenuator and the gain may apply different attenuation factors and gain factors based on the dynamic range of the voltage sensor.

In embodiments, the main measurement circuitry may be used to measure voltage and current values and the redundant measurement circuitry may be used to confirm and/or check errors in the voltage and current values measured by the main measurement circuitry. The measurement values from the main measurement circuitry may also be used to confirm and check errors in the measurement values from the redundant measurement circuitry. In this case, the redundant measurement circuitry assumes the role of the main measurement circuitry and the main measurement circuitry assumes the role of the redundant measurement circuitry. In other words, the main and redundant measurement circuitry may change roles.

Figure 5A:
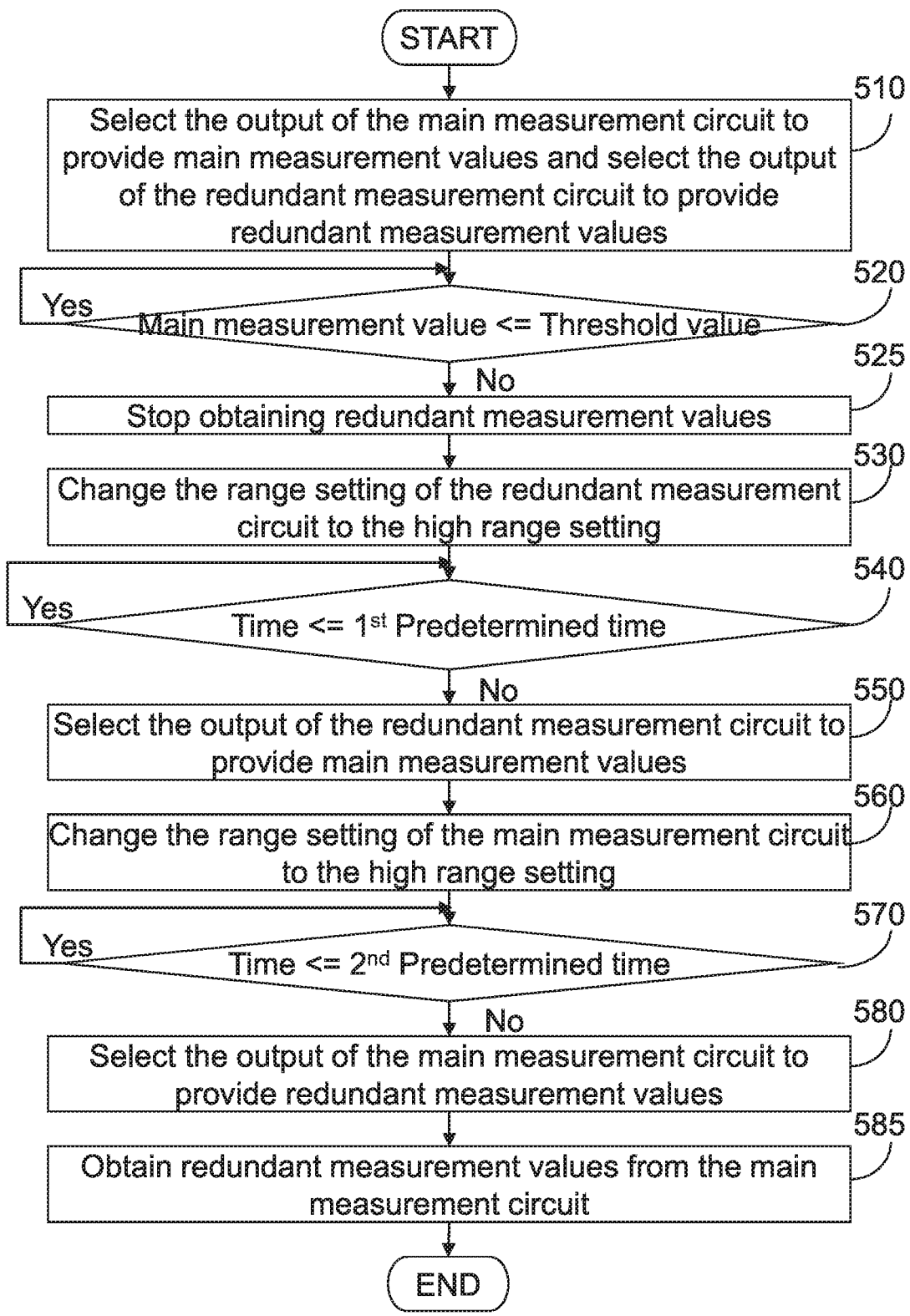
FIGS. 5A-7 are flowcharts of methods of continuously measuring voltage and current while changing range settings of the measurement circuitry of FIG. 4 in accordance with embodiments of the present disclosure.

FIG. 5A is a flowchart illustrating a method of measuring sensed voltage and current continuously during transient periods when the range settings of the measurement circuitry are changed. As described above, devices that require accurate and failsafe sensor measurements, such as electrosurgical generators, include main and redundant sensors. The voltage and current sensed by the redundant voltage and current sensors may be checked periodically to verify that the main voltage and current sensors are working properly. The method according to the present disclosure uses redundant measurement circuits before, during, and/or after transient periods when the range settings of the main measurement circuits are changed, to obtain continuous and accurate sensor measurements. This method may be implemented by using a combination of digital and analog circuits.

When an electrosurgical procedure is started, electrosurgical energy is generated and provided to tissue. The main and redundant sensors sense analog waveforms of the electrosurgical energy and provide sensor signals to the main and redundant measurement circuits. In step 510, a main measurement circuit is selected to provide main measurement values based on sensor signals from a main sensor to the main measurement channel, and a redundant measurement circuit is selected to provide redundant measurement values based on sensor signals from a redundant sensor to the redundant measurement channel. As described above, the redundant measurement values may be used to verify the accuracy of the main measurement values. The main measurement circuit may be a main voltage measurement circuit configured to obtain voltage measurement values or a main current measurement circuit configured to obtain current measurement values. The main measurement circuit samples the sensed voltage or current waveform to obtain a digitized magnitude of the sensed voltage or current waveform, i.e., voltage or current measurement values. The voltage measurement values may be obtained from the voltage waveform sensed by the main voltage sensor and the current measurement values may be obtained from the current waveform sensed by the main current sensor.

The main measurement value is then compared to a threshold value in step 520. If it is determined that a main measurement value is less than or equal to the threshold value, then the method repeats step 520. When it is determined in step 520 that a main measurement value is greater than the threshold value, the method stops obtaining redundant measurement values in step 525, e.g., by opening switches 499a and 499b of FIG. 4, because the output from the redundant measurement circuit is not valid.

In step 530, the range setting of the redundant measurement circuit is changed from the low range setting to the high range setting, while the main measurement circuit maintains the low range setting. The main measurement circuit continues to provide main measurement values to the controller via the main measurement channel so that the controller can control the output stage based on the main measurement values.

In step 540, after the range setting of the redundant measurement circuit is changed from the low range setting to the high range setting in step 530, the time is set to zero, counted, and compared to a first predetermined time to determine whether the time has reached the first predetermined time. The first predetermined time allows for the measurement values of the redundant measurement circuit to stabilize.

If it is determined in step 540 that the time has not reached the first predetermined time, the main measurement circuit continues to provide main measurement values to the controller via the main measurement channel. If it is determined in step 540 that the time has reached the first predetermined time, the output of the redundant measurement circuit is selected to provide main measurement values to the controller via the main measurement channel, in step 550. Then, in step 560, the range setting of the main measurement circuit is changed from the low range setting to the high range setting. By selecting the output of the redundant measurement circuit to provide main measurement values via the main measurement channel after the first predetermined time, the range settings of the main measurement circuit can be changed from low to high without loss of continuous control of the electrosurgical generator by the controller.

In step 570, after the range setting of the main measurement circuit is changed from the low range setting to the high range setting in step 560, time is set to zero, counted, and compared to a second predetermined time to determine whether the time has reached the second predetermined time. The second predetermined time allows for the output of the main measurement circuit to stabilize. In embodiments, a single timer or a plurality of timers can be used to determine whether the first and second predetermined times have elapsed. Also, the first and second predetermined times in steps 540 and 570 may be same or different from each other.

If it is determined that the time has not reached the second predetermined time, the redundant measurement circuit continues to provide main measurement values to the controller in step 570 via the main measurement channel, until the time reaches the second predetermined time. If it is determined that the time reaches the second predetermined time, the output of the main measurement circuit is selected to provide redundant measurement values via the redundant measurement channel, while the redundant measurement circuit continues to provide main measurement values to the controller. Also, after it is determined that the second predetermined time has elapsed, the process obtains redundant measurement values from the main measurement circuit in step 585, e.g., by closing switches 499a and 499b of FIG. 4. As a result, the redundant measurement circuit switches its role from providing redundant measurement values to providing main measurement values while the main measurement circuit switches its role from providing main measurement values to providing redundant measurement values, so that the main measurement circuit is periodically used to verify the measurement values provided by the redundant measurement circuit.

Figure 5B:
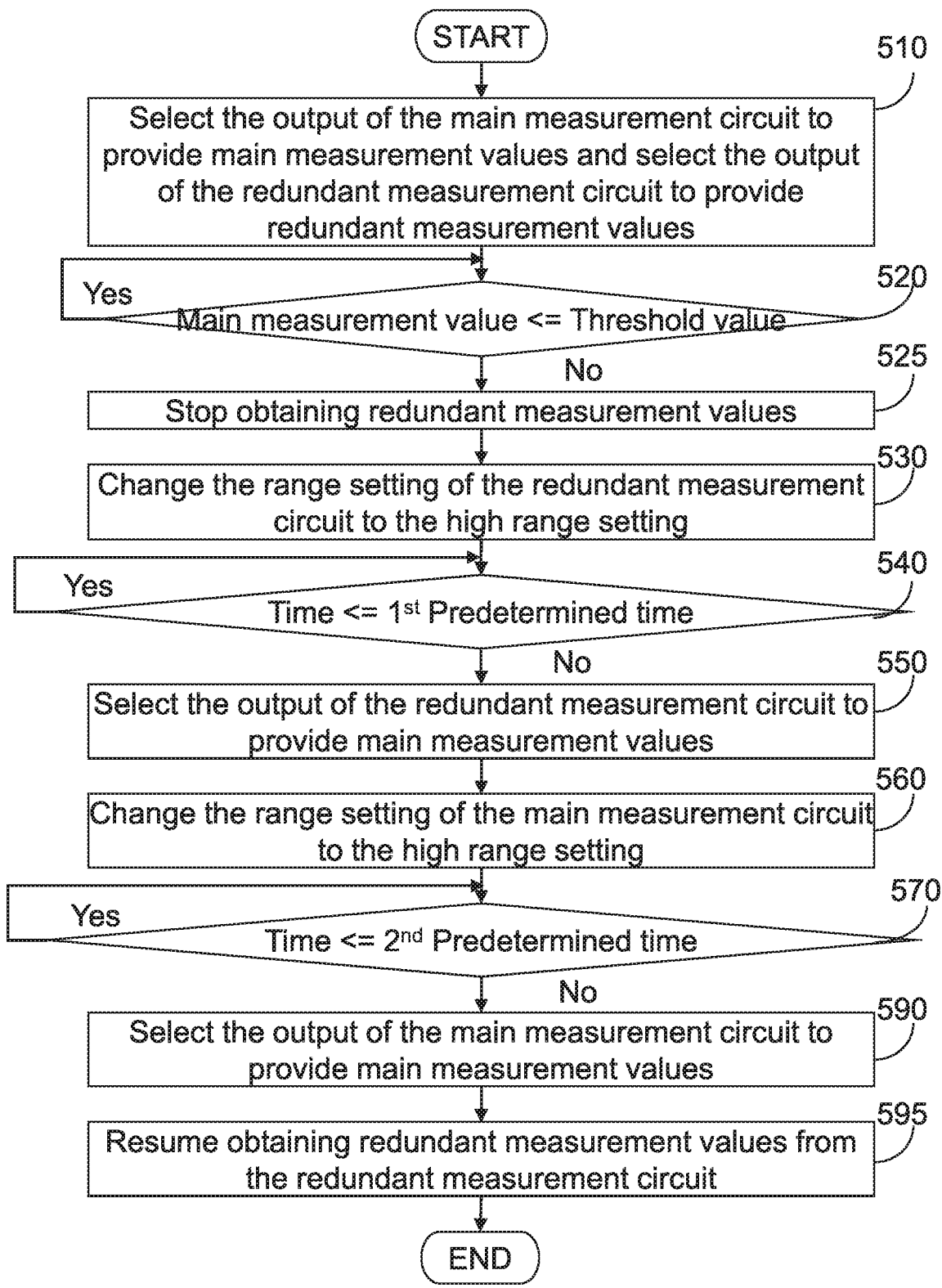

FIG. 5B is a flowchart illustrating a method of measuring voltage and current values continuously during transient periods when the range settings of the measurement circuitry are changed, in accordance with embodiments of the present disclosure. Descriptions for steps 510-570 are the same as those for steps 510-570 of FIG. 5A.

If it is determined in step 570 that the time has not reached the second predetermined time, the redundant measurement circuit continues to provide the main measurement value to the main measurement channel. Otherwise, in step 590, the output of the main measurement circuit is selected to provide the main measurement value to the controller via the main measurement channel. Then, in step 595, the process resumes obtaining redundant measurement values from the redundant measurement circuit, e.g., by closing switches 499a and 499b of FIG. 4. In other words, the redundant measurement circuit provides redundant measurement values via the redundant measurement channel and the main measurement circuit provides main measurement values via the main measurement channel so that the redundant measurement circuit is periodically used to verify the main measurement values provided by the main measurement circuit.

In some instances, the range settings of the main and redundant circuits are designed or calibrated to have some accuracy tolerance level. The main and redundant measurement circuits, however, may have differences within those accuracy tolerance levels and thus may provide different measurement values. As a result, at the time of changing from output of the main measurement circuit to the output of the redundant measurement circuit and vice versa, the voltage and current measurement values provided to the controller may have an undesirable discontinuity that would lead to inaccurate calculations of control parameters. This discontinuity problem may be solved by applying a matching scale factor as described below with respect to FIGS. 6A and 6B or by taking a weighted average of measurement values as described below with respect to FIG. 7.

Figure 6A:
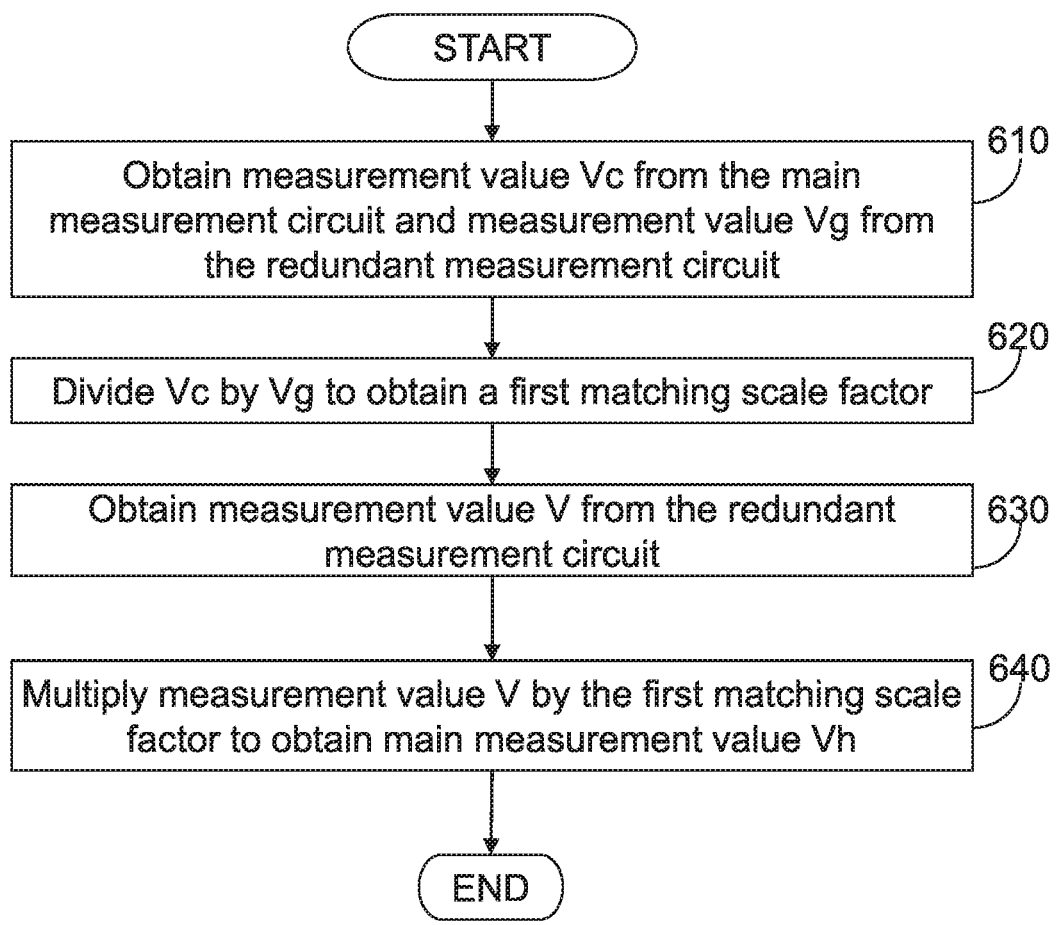

In embodiments, the steps of the flowchart of FIG. 6A may be inserted between steps 540 and 550 of FIG. 5A or 5B to address the above-described discontinuity in the voltage and current measurement values of the main and redundant measurement circuits. After it is determined that the time is greater than the first predetermined time in step 540, a measurement value $V_c$ is obtained from the main measurement circuit and a measurement value $V_g$ is obtained from the redundant measurement circuit, in step 610. Then, in step 620, a first matching scale factor is calculated by dividing the measurement value $V_c$ by the measurement value $V_g$.

In step 630, a measurement value V is obtained from the redundant measurement circuit and, in step 640, the measurement value V is multiplied by the matching scale factor to obtain a main measurement value $V_h$. Since the main measurement value $V_h$ is scaled to a value which matches or closely matches the measurement value $V_c$ from the main measurement circuit, the above-described discontinuity in the measurement values is reduced or eliminated.

The following description is an example of how the matching scale factor may be calculated to provide for continuous main measurement values when switching from the output of the main measurement circuit to the output of the redundant measurement circuit. If 49.8 V is applied to the input of the main measurement circuit, the main measurement circuit may output 50.0 V due to accuracy errors. If a threshold value for changing range settings is 50 V, then the range setting of the redundant measurement circuit is changed and the measurement circuit waits the first predetermined period for the output of the redundant measurement circuit to stabilize. After the first predetermined period, the redundant measurement circuit may output 49.9 V, while the voltage applied to the main and redundant circuits may be 50.0 V. Before switching the main measurement channel (e.g., main measurement channel 452a of FIG. 4) to the output of the redundant measurement circuit, a first matching scale factor is calculated by dividing a measurement value of the main measurement circuit by a measurement value of the redundant measurement circuit, i.e., 50.0 V/49.9 V≈1.002. After switching the output of main measurement channel to the output of the redundant measurement circuit, the measurement value of the redundant measurement circuit (i.e., 49.9 V) is multiplied by the matching scale factor (i.e., 1.002) to obtain a main measurement value of 50.0 V, which ensures that the main measurement values are continuous. Otherwise, the main measurement values would jump from the measurement value of the main measurement circuit (i.e., 50.0 V) to the measurement value of the redundant measurement circuit (i.e., 49.9 V) upon switching from the output of the main measurement circuit to the output of the redundant measurement circuit.

Figure 6B:
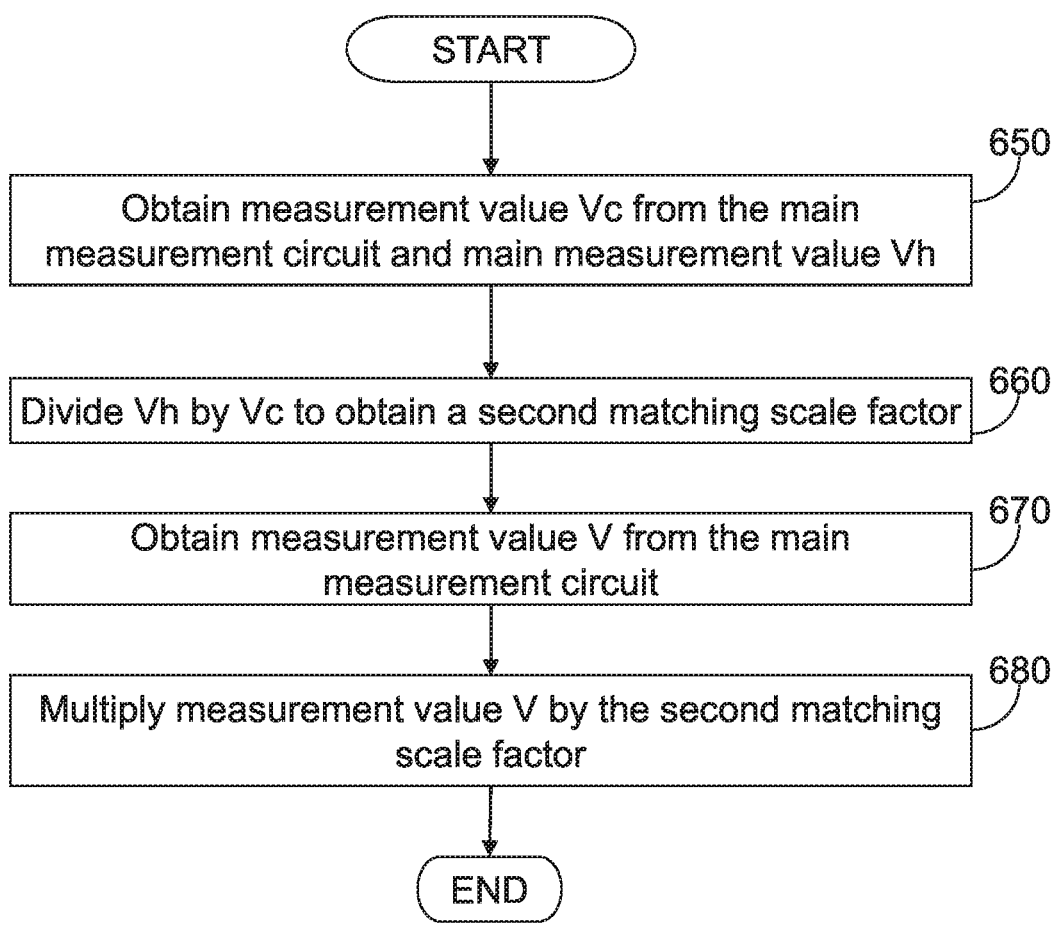

In embodiments, the steps of the flowchart of FIG. 6B may be inserted between steps 570 and 590 of FIG. 5B to address the discontinuity in the main measurement values when switching the main measurement channel from the output of the redundant measurement to the output of the main measurement circuit as described above. Before switching the main measurement channel to the output of the main measurement circuit, a measurement value $V_c$ from the main measurement circuit and the main measurement value $V_h$ are obtained in step 650. In step 660, a second matching scale factor is calculated by dividing the main measurement value $V_h$ by the measurement value $V_c$.

In step 670, a measurement value is obtained from the main measurement circuit and, in step 680, the measurement value obtained from the main measurement circuit is multiplied by the second matching scale factor to obtain a main measurement value. Since the measurement value is scaled to a value, which matches or closely matches the measurement value from the redundant measurement circuit, which is equal to $V_g$ times the first scale factor, the above-described discontinuity in the measurement values is reduced or eliminated.

The following description is an example of how a second matching scale factor may be calculated to provide continuous main measurement values when switching the main measurement channel from the output of the redundant measurement circuit back to the output of the main measurement circuit. If 50.5 V is applied to the input of the redundant measurement circuit and the input of the main measurement circuit, the redundant measurement circuit may output 50.3 V and the main measurement value $V_h$ may be 50.4 V after multiplying the measurement value of the redundant measurement circuit by the first matching scale factor, while the main measurement circuit may output 50.6 V. If, after the second predetermined time has elapsed, the main measurement channel is switched from the output of the redundant measurement circuit to the output of the main measurement circuit, the main measurement value may jump from 50.4 V to 50.6 V. To reduce or eliminate this discontinuity in the main measurement value, the second matching scale factor is calculated by dividing the measurement value of the main measurement circuit by the measurement value of the main measurement circuit (i.e., 50.4 V/50.6 V≈0.998). Then, after the main measurement channel is switched back to the output of the main measurement circuit, the measurement value of the main measurement circuit (i.e., 50.6 V) is multiplied by the second matching scale factor (i.e., 0.998) so that the main measurement value remains at 50.4 V.

Figure 7:
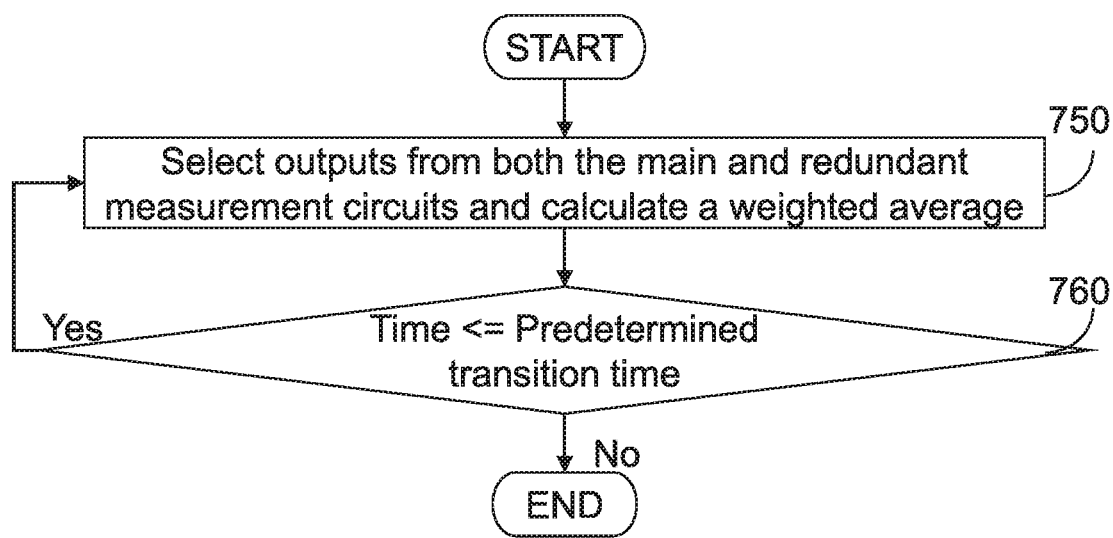

FIG. 7 is a flowchart illustrating a method for smoothly transitioning between the main measurement values output from the main measurement circuit and the main measurement values output from the redundant measurement circuit according to another embodiment of the present disclosure. The steps of the flowchart of FIG. 7 may be inserted between steps 540 and 550 of FIG. 5A or 5B to solve the above-described discontinuity problem when switching between the main and redundant measurement circuits.

After the first predetermined time has elapsed, a weighted average for transitioning to the output of the redundant measurement circuit is calculated in step 750. In order to calculate the weighted average, measurement values from both the main and redundant measurement circuits are processed to obtain measurement value $V_c$ from the main measurement circuit and measurement value $V_g$ from the redundant measurement circuit. Time t is counted from zero to a predetermined transition time $T_x$, e.g., a period for smoothly transitioning from measurement values output from the main measurement circuit to measurement values output from the redundant measurement circuit. The weighted average is calculated as follows:

$$V_R = V_c \times (1-x) + V_g \times x,$$

where $V_R$ is the weighted average for transitioning from measurement values output from the main measurement circuit to measurement values output from the redundant measurement circuit and x is $$\frac{t}{T_x}$$

for t=0 to t=$T_x$, and $V_R = V_R$ for t≥$T_x$. Thus, when time t is zero, the weighted average is the measurement value output from the main measurement circuit, and, when time t reaches the predetermined transition time $T_x$, the weighted average is the measurement value output from the redundant measurement circuit. In this way, the weighted average can provide a smooth transition from the measurement values output from the main measurement circuit to the measurement values output from the redundant measurement circuit.

In step 760, it is determined whether the predetermined transition time $T_x$ has elapsed. If the predetermined transition time $T_x$ has not elapsed, the method continues to perform step 750. When the time reaches the predetermined transition time $T_x$, the process for smoothly transitioning between the main measurement values output from the main measurement circuit and the main measurement values output from the redundant measurement circuit ends.

In embodiments, a process similar to the process of FIG. 7 may be performed when transitioning from main measurement values output from the redundant measurement circuit to main measurement values output from the main measurement circuit, e.g., in the case where the main and redundant measurement circuits exchange roles. In these embodiments, to calculate the weighted average, the measurement values output from both the main and the redundant measurement circuits are processed to obtain measurement value $V_c$ from the output of the main measurement circuit and to obtain measurement value $V_g$ from the output of the redundant measurement circuit. Time t is counted from zero to a predetermined transition time $T_x$, e.g., a period during which there is a smooth transition from the measurement values output from the redundant measurement circuit to the measurement values output from the main measurement circuit. The weighted average is calculated as follows:

$$V_M = V_c \times x + V_g \times (1-x),$$

where $V_M$ is the weighted average, x is $$\frac{t}{T_x}$$

for t=0 to t=$T_x$, and $V_M = V_c$ for t≥$T_x$. Thus, when time t is zero, the weighted average is the measurement value output from the redundant measurement circuit and, when time t reaches the predetermined transition time $T_x$, the weighted average is the measurement value output from the main measurement circuit. In this way, the weighted average $V_M$ can provide a smooth transition from the measurement values output from the redundant measurement circuit to the measurement values output from the main measurement circuit during the predetermined transition time $T_x$.

In embodiments, the predetermined transition time for transitioning from the measurement values output from the main measurement circuit to the measurement values output from the redundant measurement circuit can be the same as or different from the predetermined transition time for transitioning from the measurement values output from the redundant measurement circuit to the measurement values output from the main measurement circuit.

Although the illustrative embodiments of the present disclosure have been described herein with reference to the accompanying drawings, it is to be understood that the disclosure is not limited to those precise embodiments, and that various other changes and modification may be effected therein by one skilled in the art without departing from the scope or spirit of the disclosure. For example, the steps in the flowcharts of FIGS. 5A-7 may be implemented in software, firmware, and/or hardware.

What is claimed is:

1. A measurement circuit that measures a waveform of electrical energy generated by a generator, the measurement circuit comprising:
    a sensor configured to sense a waveform having a first range of amplitudes;
    first and second circuits configured to filter the sensed waveform, each circuit including:
        an attenuator configured to amplify an amplitude of the waveform by multiplying the waveform by an attenuation factor;
        an analog-to-digital converter (ADC) configured to digitally sample the amplified waveform, which has a second range of amplitudes, to obtain digital samples;
        a gain element configured to multiply the digital samples by a gain factor; and
        a factor adjustor configured to adjust the attenuation factor and the gain factor; and
    a controller configured to calculate voltage and current of the waveform based on the digital samples and to control the generator based on the calculated voltage and current,
    wherein the first range includes and is larger than the second range.

2. The measurement circuit according to claim 1, wherein, when the amplitude reaches a predetermined threshold, the attenuator of the second circuit reduces the amplitude of the waveform and the controller obtains the digital samples from the second circuit.

3. The measurement circuit according to claim 2, wherein the controller does not obtain the digital samples from the first circuit.

4. The measurement circuit according to claim 2, wherein the attenuator of the first circuit reduces the amplitude of the sensed waveform after a predetermined time has elapsed after the attenuator of the second circuit reduces the amplitude of the sensed waveform.

5. The measurement circuit according to claim 4, wherein the controller includes a matching scale factor gain element configured to calculate a weighted average of the voltage and current based on the digital samples from the first and second circuits, during the predetermined time.

6. The measurement circuit according to claim 4, wherein the controller obtains the digital samples from the first circuit after the predetermined time has elapsed.

7. The measurement circuit according to claim 6, wherein the controller does not obtain the digital samples from the second circuit.

8. The measurement circuit according to claim 2, wherein the reduced amplitude is within the second range.

9. The measurement circuit according to claim 1, wherein the attenuation factor and the gain factor are adjusted so that the product of the attenuation factor and the gain factor is one.

10. The measurement circuit according to claim 1, wherein the controller includes a selector configured to select between the first circuit and the second circuit to obtain the digital samples.

11. A method for measuring a waveform of electrical energy generated by a generator, the method comprising:
    sensing a waveform having a first range of amplitudes;
    filtering the sensed waveform by first and second circuits, wherein filtering the sensed waveform includes:
        amplifying an amplitude of the waveform by multiplying the amplitude by an attenuation factor;
        digitally sampling the amplified waveform, which has a second range of amplitudes, to obtain digital samples;
        adjusting the attenuation factor and a gain factor; and
        multiplying the digital samples by the gain factor;
    calculating voltage and current of the waveform based on the digital samples; and
    controlling the generator based on the calculated voltage and current,
    wherein the first range includes and is larger than the second range.

12. The method according to claim 11, wherein, when the amplitude reaches a predetermined threshold:
    amplifying the amplitude of the sensed waveform includes reducing the amplitude of the waveform from the second circuit, and
    the digital samples are obtained from the second circuit.

13. The method according to claim 12, wherein the digital samples are not obtained from the first circuit.

14. The method according to claim 12, wherein the amplitude of the sensed waveform is reduced by the first circuit after a predetermined time has elapsed after the amplitude of the sensed waveform is reduced by the second circuit.

15. The method according to claim 14, wherein controlling the generator includes calculating a weighted average of the voltage and current based on the digital samples from the first and second circuits, during the predetermined time.

16. The method according to claim 14, wherein the digital samples are obtained from the first circuit after the predetermined time has elapsed.

17. The method according to claim 16, wherein the digital samples are not obtained from the second circuit after the predetermined time has elapsed.

18. The method according to claim 12, wherein the reduced amplitude is within the second range.

19. The method according to claim 11, wherein the attenuation factor and the gain factor are adjusted so that the product of the attenuation factor and the gain factor is one.

20. The method according to claim 11, wherein controlling the generator includes selecting between the first circuit and the second circuit to obtain the digital samples.

* * * * *